(12) United States Patent
Prior et al.

(10) Patent No.: US 10,918,409 B2
(45) Date of Patent: Feb. 16, 2021

(54) MORCELLATOR WITH AUGER TISSUE FEEDER

(71) Applicant: Covidien LP, Mansfield, MA (US)

(72) Inventors: Scott J. Prior, Shelton, CT (US);
Danial P. Ferreira, Shelton, CT (US);
Henry E. Holsten, Hamden, CT (US);
Stanislaw Kostrzewski, Newtown, CT (US)

(73) Assignee: Covidien LP, Mansfield, MA (US)

( * ) Notice: Subject to any disclaimer, the term of this patent is extended or adjusted under 35 U.S.C. 154(b) by 289 days.

(21) Appl. No.: 16/208,759

(22) Filed: Dec. 4, 2018

(65) Prior Publication Data

US 2019/0167291 A1 Jun. 6, 2019

Related U.S. Application Data (60) Provisional application No. 62/594,600, filed on Dec. 5, 2017.

(51) Int. Cl.
*A61B 17/32* (2006.01)
*A61B 17/3207* (2006.01)
*A61B 17/00* (2006.01)
*A61B 17/34* (2006.01)

(52) U.S. Cl.
CPC .. *A61B 17/32002* (2013.01); *A61B 17/00234* (2013.01); *A61B 17/320758* (2013.01); *A61B 17/3423* (2013.01); *A61B 17/3462* (2013.01); *A61B 2017/00287* (2013.01); *A61B 2017/00349* (2013.01); *A61B 2017/00353* (2013.01); *A61B 2017/320024* (2013.01);
(Continued)

(58) Field of Classification Search
CPC ...... A61B 17/320758; A61B 17/32002; A61B 2017/320032; A61B 17/320024; A61B 2017/320775
See application file for complete search history.

(56) References Cited

U.S. PATENT DOCUMENTS

| 4,729,763 A | * | 3/1988 | Henrie | A61B 17/320758 |
| | | | | 604/22 |
| 4,883,458 A | * | 11/1989 | Shiber | A61B 8/12 |
| | | | | 604/22 |
| 4,935,025 A | | 6/1990 | Bundy et al. | |
| (Continued) | | | | |

FOREIGN PATENT DOCUMENTS

| EP | 0806183 A1 | 11/1997 |
| GB | 2327350 A | 1/1999 |
| (Continued) | | |

*Primary Examiner* — Wade Miles
(74) *Attorney, Agent, or Firm* — Carter, DeLuca & Farrell LLP (57) ABSTRACT

A morcellator include a housing, a knife, and a first auger. The housing defies a longitudinal axis and has an inner wall that defines a passage along the longitudinal axis. The knife is disposed about an inner wall of the housing and is secured to a distal portion of the housing. The knife extends distally from the distal portion of the housing. The first auger is disposed within the housing and has a first auger shaft and a first auger blade. The first auger shaft extends in a direction parallel to the longitudinal axis of the housing. The first auger is configured to rotate relative to the housing such that the first auger blade moves tissue proximally through the passage.

19 Claims, 5 Drawing Sheets

(52) U.S. Cl.
CPC ............. *A61B 2017/320064* (2013.01); *A61B 2017/320775* (2013.01); *A61B 2017/347* (2013.01); *A61B 2017/3466* (2013.01)

(56) References Cited

U.S. PATENT DOCUMENTS

| | | | |
|---|---|---|---|
| 5,403,276 A | 4/1995 | Schechter et al. | |
| 5,443,472 A | 8/1995 | Li | |
| 5,520,634 A | 5/1996 | Fox et al. | |
| 5,569,284 A | 10/1996 | Young et al. | |
| 5,591,187 A * | 1/1997 | Dekel | A61B 17/32002 606/170 |
| 5,618,296 A | 4/1997 | Sorensen et al. | |
| 5,653,696 A * | 8/1997 | Shiber | A61B 17/22012 604/267 |
| 5,669,927 A | 9/1997 | Boebel et al. | |
| 5,746,760 A | 5/1998 | Humphrey, Jr. | |
| 5,916,198 A | 6/1999 | Dillow | |
| 6,039,748 A | 3/2000 | Savage et al. | |
| 6,045,566 A | 4/2000 | Pagedas | |
| 6,162,235 A | 12/2000 | Vaitekunas | |
| 6,468,228 B1 | 10/2002 | Topel et al. | |
| D535,748 S | 1/2007 | Wolf | |
| 7,156,839 B2 | 1/2007 | Bayer et al. | |
| 7,232,439 B2 | 6/2007 | Ciarrocca | |
| 7,850,684 B2 | 12/2010 | Marshall et al. | |
| 8,025,656 B2 | 9/2011 | Gruber et al. | |
| 8,100,928 B2 | 1/2012 | Nohilly et al. | |
| 8,152,820 B2 | 4/2012 | Mohamed et al. | |
| 8,308,746 B2 | 11/2012 | Pravong et al. | |
| 8,343,148 B2 | 1/2013 | Fleming et al. | |
| 8,608,764 B2 | 12/2013 | Ambardekar | |
| 8,652,156 B2 | 2/2014 | Holdgate et al. | |
| 9,539,018 B2 | 1/2017 | Sartor et al. | |
| 9,603,624 B2 | 3/2017 | Sartor et al. | |
| 9,913,653 B2 | 3/2018 | Sartor et al. | |
| 2005/0261676 A1 | 11/2005 | Hall et al. | |
| 2006/0089527 A1 | 4/2006 | Doll | |
| 2008/0039880 A1 | 2/2008 | Nohilly et al. | |
| 2008/0039883 A1 | 2/2008 | Nohilly | |
| 2008/0058846 A1 | 3/2008 | Vosough | |
| 2008/0065129 A1 | 3/2008 | Batchelor et al. | |
| 2008/0103412 A1 | 5/2008 | Chin | |
| 2008/0135780 A1 | 6/2008 | Giering et al. | |
| 2008/0255597 A1 | 10/2008 | Pravong | |
| 2009/0292281 A1 | 11/2009 | Fleming | |
| 2010/0305566 A1 | 12/2010 | Rosenblatt et al. | |
| 2011/0184409 A1 | 7/2011 | Jenkins et al. | |
| 2011/0257651 A1 | 10/2011 | Jenkins | |
| 2011/0264129 A1 | 10/2011 | Holdgate | |
| 2012/0016399 A1 | 1/2012 | Poulsen | |
| 2012/0078038 A1 | 3/2012 | Sahney | |
| 2013/0090642 A1 | 4/2013 | Shadduck et al. | |
| 2013/0123797 A1 * | 5/2013 | Livneh | A61B 17/22031 606/114 |
| 2013/0218186 A1 | 8/2013 | Dubois et al. | |
| 2014/0276840 A1 * | 9/2014 | Richter | A61B 17/1659 606/80 |
| 2015/0141869 A1 | 5/2015 | Costello et al. | |
| 2015/0335342 A1 | 11/2015 | Hart et al. | |
| 2016/0022883 A1 * | 1/2016 | Guru | A61B 17/32002 604/319 |
| 2016/0256174 A1 * | 9/2016 | Davis | A61B 17/1659 |
| 2018/0078276 A1 * | 3/2018 | Chen | A61B 10/0266 |
| 2018/0256196 A1 * | 9/2018 | Nishio | A61B 17/320725 |
| 2018/0280045 A1 * | 10/2018 | Malhi | A61B 17/22031 |

FOREIGN PATENT DOCUMENTS

| | | |
|---|---|---|
| GB | 2327351 A | 1/1999 |
| WO | 2009141579 A1 | 11/2009 |
| WO | 2014123571 A1 | 8/2014 |

\* cited by examiner

MORCELLATOR WITH AUGER TISSUE FEEDER

CROSS-REFERENCE TO RELATED APPLICATION

This application claims the benefit of, and priority to, U.S. Provisional Patent Application Ser. No. 62/594,600, filed Dec. 5, 2017, the entire contents of which are hereby incorporated by reference.

BACKGROUND

1. Technical Field

The present disclosure relates to tissue morcellation and, more specifically, to tissue morcellators which can be used for partial or total removal of body tissue or organs from a body cavity.

2. Discussion of Related Art

In minimally invasive surgical procedures, operations are carried out within the body by using elongated instruments inserted through small entrance openings in the body. The initial opening in the body tissue to allow passage of instruments to the interior of the body may be a natural passageway of the body, or it can be created by a tissue-piercing instrument such as a trocar, or by a small incision into which a cannula is inserted.

Minimally invasive procedures may be used for partial or total removal of body tissue or organs from a body cavity, e.g. partial or total hysterectomy, myomectomy, nephrectomy, cholecystectomy, lobectomy, and other procedures including thoracic, abdominal, laparoscopic, and endoscopic procedures. During such procedures, it is common that a cyst, fibroid, myoma, tumor, or other affected tissue or organ needs to be removed via the access opening or through a cannula. Various types of entrapment devices have been disclosed to facilitate this procedure. In many procedures where cancerous tumors are removed, removal of the specimen in an enclosed environment, e.g., a specimen bag, is highly desirable to inhibit seeding of cancer cells (i.e., portions of cancer cells contacting healthy tissue).

Several minimally invasive surgical procedures require the bulk removal of body tissue or organs through a limited surgical opening. As such, the tissue needs to be morcellated within the body cavity into smaller pieces of tissue to facilitate removal.

There is a continuing need for morcellators for bulk removal of tissue. In addition, there is a continuing need for morcellators that do not damage or penetrate a specimen bag during morcellation procedures.

SUMMARY

In an aspect of the present disclosure, a morcellator include a housing, a knife, and a first auger. The housing defines a longitudinal axis and has an inner wall that defines a passage along the longitudinal axis. The knife is disposed about an inner wall of the housing and is secured to a distal portion of the housing. The knife extends distally from the distal portion of the housing. The first auger is disposed within the housing and has a first auger shaft and a first auger blade. The first auger shaft extends in a direction parallel to the longitudinal axis of the housing. The first auger is configured to rotate relative to the housing such that the first auger blade moves tissue proximally through the passage.

In aspects, a distal end of the first auger is positioned proximal of a distal end of the knife. The housing may include a shield that extends distally beyond the knife. The shield may be configured guide tissue into the passage.

In aspects, the morcellator may include a second auger that is disposed within the housing. The second auger may have a second auger shaft and a second auger blade. The second auger shaft may be parallel to the first auger shaft. The passage of the housing may have an ovular cross-section with a first dimension equal to diameters of the first and second augers and a second dimension less than the sum of the diameters of the first and second augers with the second dimension being perpendicular to the first dimension. The first and second auger blades may have opposite pitches such that as the first auger and second auger are rotated in opposite directions about a respective auger shaft, the first and second augers are configured to draw tissue proximally through the passage. The first and second auger blades may be windowed relative to one another and positioned such that the longitudinal axis of the housing passes through each of the first and second auger blades.

In some aspects, the morcellator includes a third auger and a fourth auger. The third auger may have a third auger shaft and a third auger blade. The third auger shaft may be parallel to the first auger shaft. The third auger may be positioned adjacent the second auger and on an opposite side of the housing from the first auger. The fourth auger may have a fourth auger shaft and a fourth auger blade. The fourth auger shaft may be parallel to the first auger shaft. The fourth auger may be positioned adjacent the first and third auger shafts and on an opposite side of the housing from the second auger. The first, second, third, and fourth auger blades are spaced apart from one another are and are pitched in the same direction such that rotation of each of the first, second, third, and fourth augers in the same direction about a respective auger shaft is configured to draw tissue proximally through the passage.

In another aspect of the present disclosure, a method of morcellating tissue includes rotating a housing of a morcellator about a longitudinal axis of the housing and engaging tissue with the rotating auger to draw tissue proximally through the passage. The housing has an inner surface that defines a passage therethrough and including a spiral projection that extends inward from the inner surface to form an auger.

In aspects, engaging tissue with the rotating auger includes passing a tool through the passage to engage tissue distal of the housing and drawing the tissue proximally into the auger. Engaging tissue with the tool may include rotating a threaded portion of the tool in a first direction into the tissue and engaging tissue with the rotating auger may include rotating the auger in a second direction opposite of the first direction. Rotating the housing may include rotating an elongate shaft that extends distally from a handle to rotate the housing. The housing may be rotatably fixed to a distal portion of the elongate shaft.

In another aspect of the present disclosure, a morcellator includes a housing that defines a longitudinal axis and has an inner surface that defines a passage along the longitudinal axis. The housing may include a spiral projection that extends inward form the inner surface to form an auger. The housing is configured to rotate about the longitudinal axis such that the auger draws tissue proximally through the passage.

In aspects, the housing has a proximal end and a distal end. The housing may be tapered from the distal end towards the proximal end.

In some aspects, the morcellator includes an elongate shaft that has a distal portion which supports the housing. The housing may be rotatably fixed to the distal portion of the elongate shaft. The morcellator may include a handle with the elongate shaft extending distally from the shaft. The handle may be configured to rotate the elongate shaft relative to the handle to rotate the housing about the longitudinal axis.

In another aspect of the present disclosure, a method of morcellating tissue includes engaging tissue with a distal portion of a housing of a morcellator until the tissue is in contact with an auger disposed within a passage defined by the housing, rotating the auger to draw tissue proximally through the passage of the housing, and severing a portion of tissue from the rest of the tissue with a knife disposed about a distal portion of the housing, the knife extending distally beyond the auger.

In aspects, engaging the tissue with the distal portion of the housing includes engaging the tissue with a shield of the housing, the shield extending distally past the knife. Engaging the tissue with the shield may include the shield guiding tissue towards the auger.

In some aspects, severing a portion of the tissue includes skiving the portion of the tissue from an outer surface of the tissue.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

Figure 1:
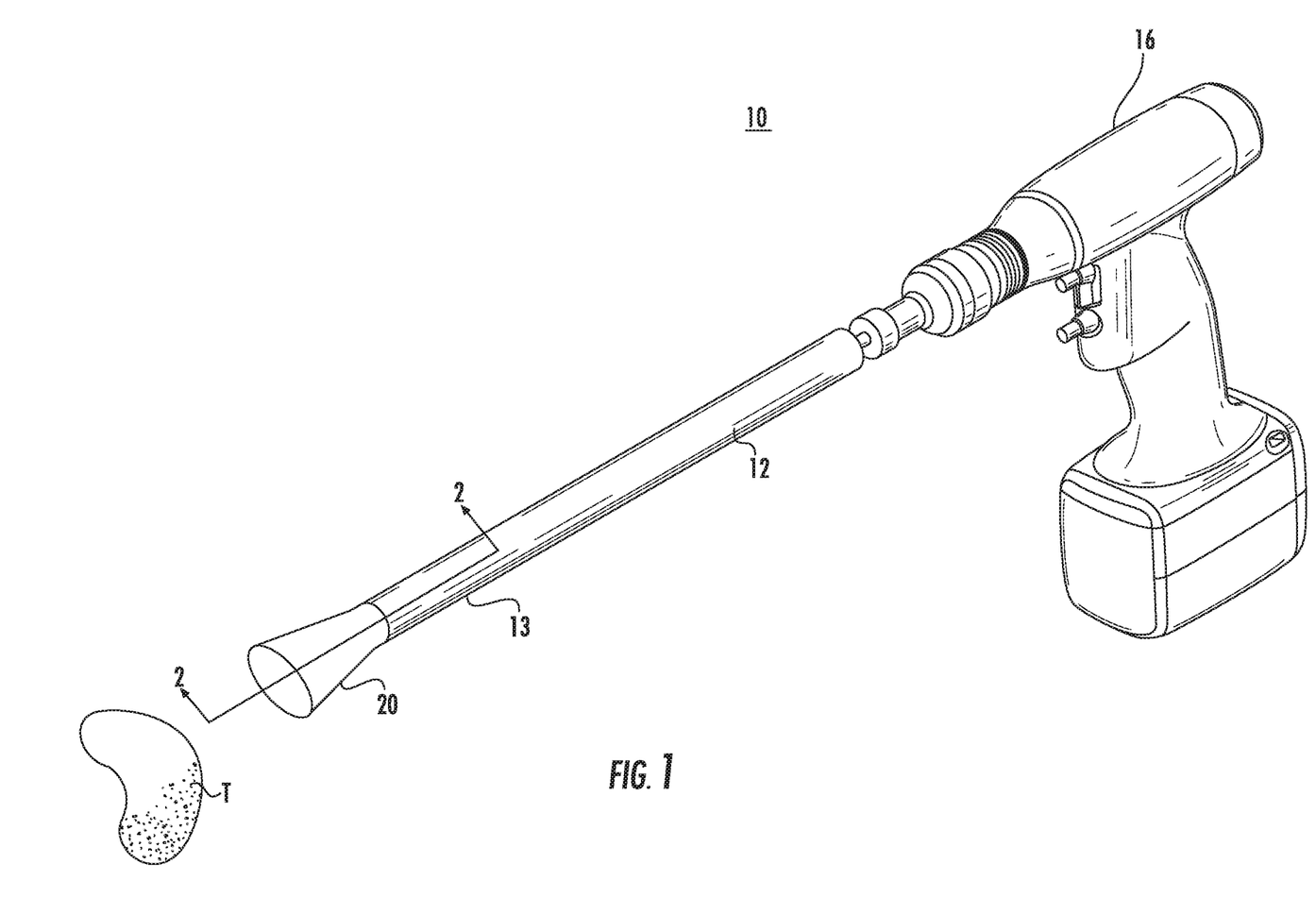
FIG. 1 is a perspective view of a morcellator provided in accordance with the present disclosure.
Figure 2:
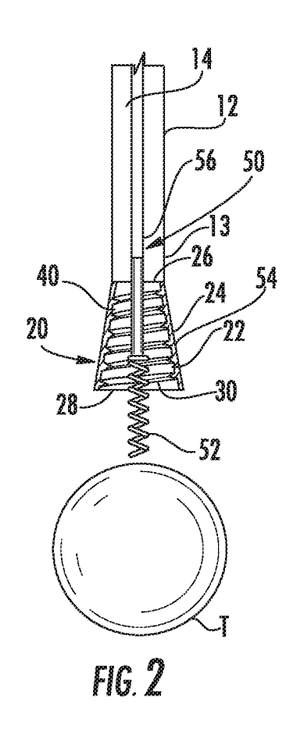
FIG. 2 is a side, partial, cross-sectional view taken along section line 2-2 of FIG. 1 illustrating a housing of the morcellator with a tool passed through a passage of the housing.

Referring now to FIGS. 1 and 2, a morcellator 10 is provided in accordance with the present disclosure. The morcellator 10 includes a housing 20 that defines a passage 30 therethrough. The morcellator 10 may also include an elongate shaft 12 defining a channel 14 in communication with the passage 30. A tool or threaded shaft 50 may be inserted through the handle 16 and the channel 14 to draw tissue into the morcellator as detailed below. The housing 20 can be rotatably or fixedly secured to a distal portion 13 of the elongate shaft 12. The morcellator 10 may include a handle 16 secured to a proximal portion of the elongate shaft 12. The handle 16 may be configured to rotate the elongate shaft 12 relative to the handle 16 and/or to rotate the housing 20 relative to the elongate shaft 12. The handle 16 may be a powered handle such that the handle 16 electromechanically rotates the elongate shaft 12 and/or the housing 20 or may be a manual handle allowing a clinician to manually rotate the elongate shaft 12 and/or the housing 20. Similarly, the threaded shaft 50 may also be electromechanically or manually manipulated by the handle 16. In some embodiments, the housing 20 is electromechanically manipulated and the threaded shaft 50 is manually manipulated. For a detailed description of exemplary powered or manually handles reference can be made to U.S. Patent Publication No. 2015/0141869 and U.S. Pat. No. 9,603,624, the entire contents of each of these disclosures are hereby incorporated by reference.

With particular reference to FIG. 2, the housing 20 has an inner surface 22 and an outer surface 24 that extend between an open proximal end 26 and an open distal end 28 of the housing 20. The housing 20 tapers from the distal end 28 to the proximal end 26 such that the housing 20 is generally frustoconical in shape. The outer surface 24 of the housing 20 is relatively smooth such that the housing 20 can rotate within structures, e.g., a body cavity or a specimen bag, without damaging a structure in contact with the outer surface 24 of the housing 20. The inner surface 22 includes an auger 40 in the form of a thread that extends from the inner surface 22 inwardly towards a center of the passage 30.

The auger 40 is in the form of a continuous projection from the inner surface 22 that spirals about the inner surface 22 between the proximal end 26 and the distal end 28 of the housing 20 in a first direction, e.g., clockwise. The auger 40 is pitched to draw tissue proximally through the passage 30 in response to rotation of the housing 20 in the first direction. The projection of the auger 40 is sharpened such that the auger 40 is configured to engage or bite into tissue disposed within the passage 30. It is envisioned that the auger 40 may cut or tear tissue disposed within the passage 30. The auger 40 may extend all the way to each of the proximal and distal ends 26, 28 or may be spaced apart from one or both of the proximal and distal ends 26, 28. Spacing the auger 40 away from the distal end 28 of the housing 20 may prevent the auger 40 from contacting and/or damaging tissue or specimen bags within a body cavity. In addition, spacing the auger 40 from the distal end 28 of the housing 20 may prevent the auger 40 from unintentionally harming a clinician handling the morcellator 10.

The morcellator 10 may also include a grasper or threaded shaft 50 that is insertable through the channel 14 and the passage 30 such that the threaded shaft 50 passes entirely through the housing 20. The thread shaft 50 includes a threaded distal portion 52 that is in the form of a cork screw that spirals in a second direction opposite the first direction, e.g., counter-clockwise. The threaded shaft 50 may include a stop 54 (FIG. 3) at a proximal end of the threaded distal portion 52 that has a diameter larger than a proximal portion 56 of the threaded shaft 50.

Figure 3:
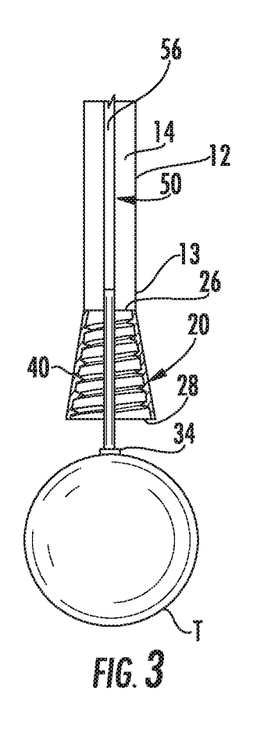
FIG. 3 is a side, partial, cross-sectional view of the housing of FIG. 2 with a threaded portion of the tool disposed in tissue.

With reference to FIGS. 2-5, use of the morcellator 10 for morcellating tissue is disclosed in accordance with the present disclosure. Initially referring to FIG. 2, the threaded shaft 50 is passed through the housing 20 such that the threaded distal portion 52 extends from the distal end 28 of the housing 20. The housing 20 may be positioned within a specimen bag that forms a seal about a portion of the morcellator proximal of the housing 20. The threaded distal portion 52 of the threaded shaft 50 is then brought into contact with tissue "T" to be morcellated. The threaded shaft 50 is then rotated in the second direction, e.g., counter-clockwise, such that the threaded distal portion 52 engages and screws into the tissue "T" as shown in FIG. 3. The threaded shaft 50 may be rotated in the second direction until the threaded distal portion 52 is fully disposed within the tissue "T" and the tissue "T" is abutted by the stop 54. As the threaded distal portion 52 is rotated into the tissue "T," the threaded shaft 50 maybe advanced distally through the housing 20. It is envisioned that when a length of the tissue "T" is smaller than a length of the threaded distal portion 52 that the threaded distal portion 52 may not be fully disposed within the tissue "T" such that the tissue "T" is not abutted by the stop 54 or that the threaded distal portion 52 extends distally through the tissue "T" when the tissue "T" is abutted by the stop 54.

Figure 4:
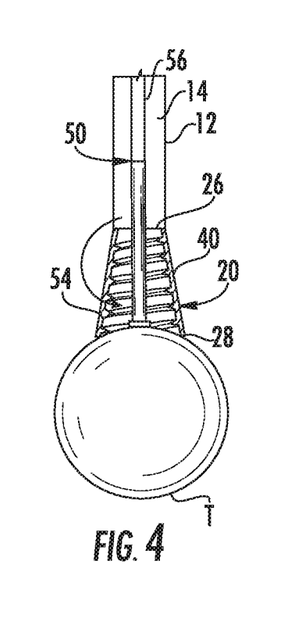
FIG. 4 is a side, partial, cross-sectional view of the housing of FIG. 2 illustrating the tool drawing the tissue into contact with an auger of the housing.

With reference to FIG. 4, with the thread distal portion 52 disposed within the tissue "T," the threaded shaft 50 is drawn proximally relative to the housing 20 such that the tissue "T" is pulled into contact with the distal end 28 of the housing 20. Prior to, as, or once the tissue "T" contacts the distal end 28 of the housing 20, the housing 20 is rotated in the first direction, e.g., clockwise, such that the auger 40 engages the tissue "T" and draws the tissue "T" proximally into the housing 20. As auger 40 engages the tissue "T," the projection of the auger 40 bites into the tissue "T." It will be appreciated that the opposing threads of the threaded distal portion 52 and the auger 40 cooperate to secure the tissue "T" on the threaded shaft 50 as the tissue "T" is drawn into the housing 20.

Figure 5:
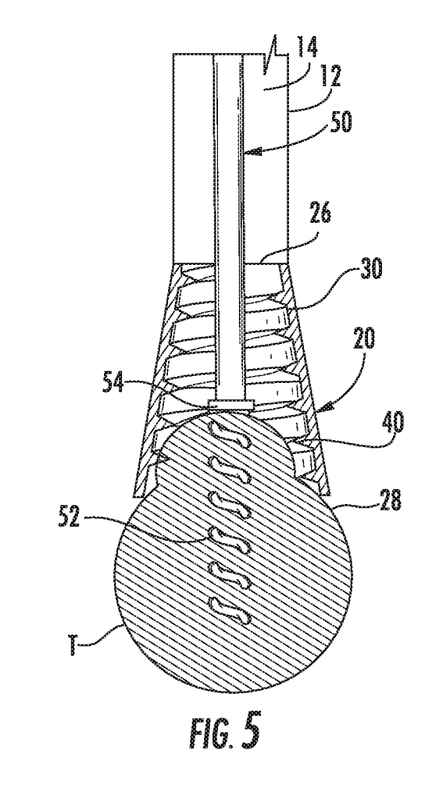
FIG. 5 is a side cross-sectional view of the housing of FIG. 2 illustrating the auger drawing the tissue proximally and compressing the tissue.

With reference to FIG. 5, as the tissue "T" is drawn into the housing 20, the tissue "T" may be compressed by the taper of the housing 20. This compression may assist the projections of the auger 40 in biting into the tissue "T" and allow the auger 40 to draw larger pieces of tissue "T" into the passage 30. As the tissue "T" is drawing through the passage 30, the size of the tissue "T' is reduced before the tissue "T" enters the channel 14 of the elongate shaft 12. As the tissue "T" is compressed the auger 40 may also tear or break up portions of the tissue "T" such that the tissue "T" can pass entirely through the channel 14 of the elongate shaft 12. More specifically, in embodiments, the auger 40 may be configured to tear the tissue "T" into one or more elongate strips of tissue "T" to facilitate passage through the channel 14. The threaded shaft 50 may be used to draw the tissue "T" through the elongate shaft 12 and out of the proximal portion of the channel 14, or other suitable exit opening, to remove the tissue "T" from the body cavity.

Figure 6:
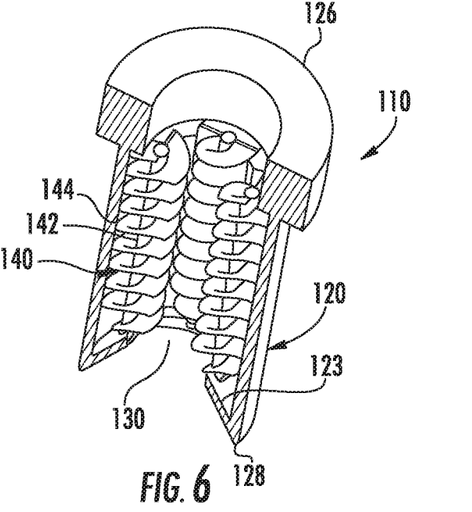
FIG. 6 is a cut-away view of a distal portion of another morcellator provided in accordance with the present disclosure.
Figure 7:
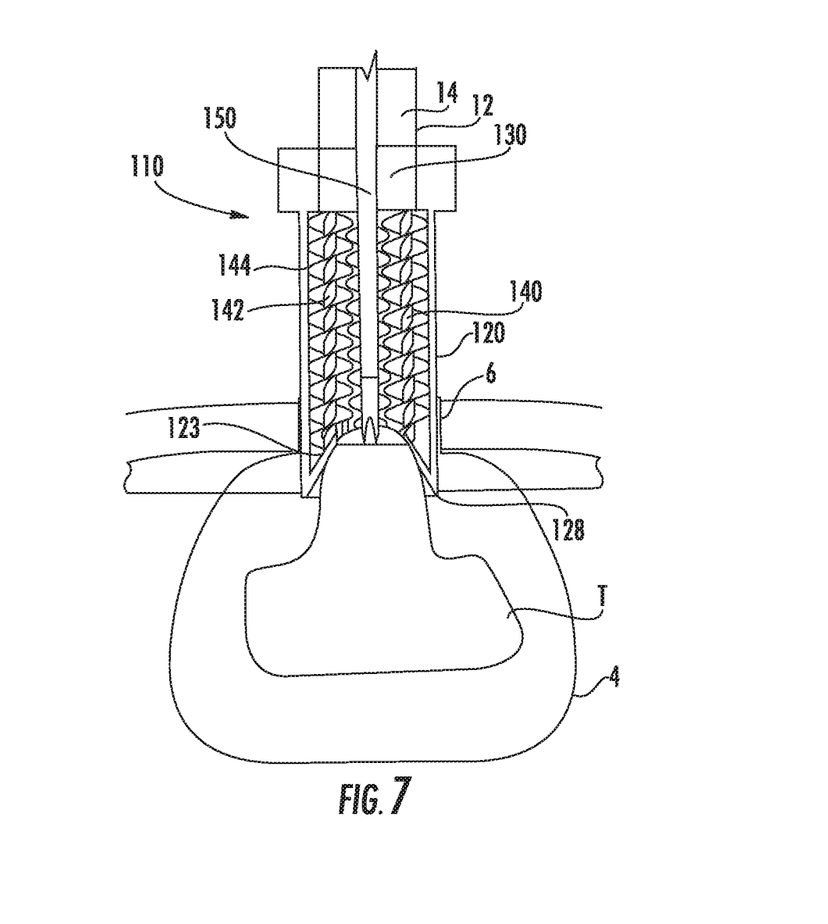
FIG. 7 is a cross-sectional view of the distal portion of the morcellator of FIG. 6 positioned within an opening, wherein a tool is engaged with tissue to draw tissue into engagement with an auger of the morcellator.

Referring to FIGS. 6 and 7, another morcellator 110 is disclosed in accordance with the present disclosure. The morcellator 110 is secured to a distal portion of the elongate shaft 12 and includes a housing 120 and augers 140. The housing 120 includes a proximal end 126 and a distal end 128 and defines a passage 130 therebetween. The passage 130 is in communication with the channel 14 of the elongate shaft 12. The housing 120 also includes a tapered guide or shield 123 that extends proximally and inward from the distal end 128 of the housing 120.

Each of the augers 140 includes an auger shaft 142 and a spiraled projection or blade 144 extending outward from the auger shaft 142. The auger shaft 142 extends in a direction parallel to a longitudinal axis of the housing 120 and is rotatably secured to the housing 120 adjacent the proximal end 126 and the distal end 128 of the housing 120. The blade 144 of each auger 140 has a continuous screw shape along a length of the auger shaft 142. Each of the blades 144 is pitched such that rotation of the auger 140 about the auger shaft 142 in a first direction draws tissue in contact with the blade 144 proximally through the passage 130 and rotation in a second direction, opposite the first direction, expels tissue in contact with the blade 144 distally from the housing 120. The first direction may be the same for each of the augers 140 or the first direction of one auger 140 may be opposite of the first direction of a second auger 140. For example, one auger may be rotated clockwise to draw tissue proximally and another auger 140 may be rotated counter-clockwise to draw tissue proximally.

Each of the auger shafts 142 is operatively associated with a handle, e.g., handle 16 (FIG. 1), such that when the handle is activated, the handle rotates each of the augers 140 about a respective one of the auger shafts 142 in the respective first direction to draw tissue in contact with the blades 144 proximally through the passage 130.

As shown, the housing 120 includes four augers 140 equally spaced about a longitudinal axis of the housing 120 with each of the augers 140 being equally sized relative to the other augers 140. It is contemplated that one or more of the augers 140 may be sized differently from the other augers 140. The augers 140 are spaced apart from one another such that the blades 144 of augers 140 do not interfere with one another as each of the augers 140 is rotated about a respective auger shaft 142. However, the augers 140 may be arranged such that each blade 144 overlaps adjacent blades 144.

With particular reference to FIG. 7, in use, the morcellator 110 is positioned within an opening in body tissue. The opening may be a natural opening or an incision. The morecellator 110 may be inserted through an access port (not shown) or the housing 120 of the morcellator 110 may function as an access port. An open end 6 of a specimen bag 4 may be secured about a distal portion of the housing 120 such that the distal end 128 of the housing is disposed within the specimen bag 4. The open end 6 of the specimen bag 4 may form a seal with an outer surface of the housing 120 such that contents of the specimen bag 4, e.g., tissue "T" to be morcellated, is isolated within a body cavity.

The tissue "T" is then brought into contact with the blades 144 of the augers 140 and the handle, e.g., handle 16 (FIG. 1), is activated to rotate the augers 144 such that the blades 144 draw the tissue "T" through the passage 130. The tissue "T" may be brought into contact with the blades 144 by pushing the distal end 128 of the housing 120 into the tissue "T" such that the tapered guide 123 of the housing 120 directs the tissue "T" into contact with the blades 144. The tapered guide 123 is configured to engage the tissue "T" while preventing the blades 144 from contacting the specimen bag 4. Additionally or alternatively, a tool 150 can be inserted through the passage 130 to engage the tissue "T" and to draw the tissue "T" proximally into contact with the blades 144. The tool 150 may also be used to draw the tissue "T" through the passage 130. As the blades 144 engage the tissue "T," the blades 144 may compress and/or tear the tissue, e.g., into one or more elongate strips of tissue "T," such that the tissue "T" passes through the passage 130 of the housing 120 and into the channel 14 of the elongate shaft 12 to remove the tissue "T" from the body cavity.

Figures 8, 9:
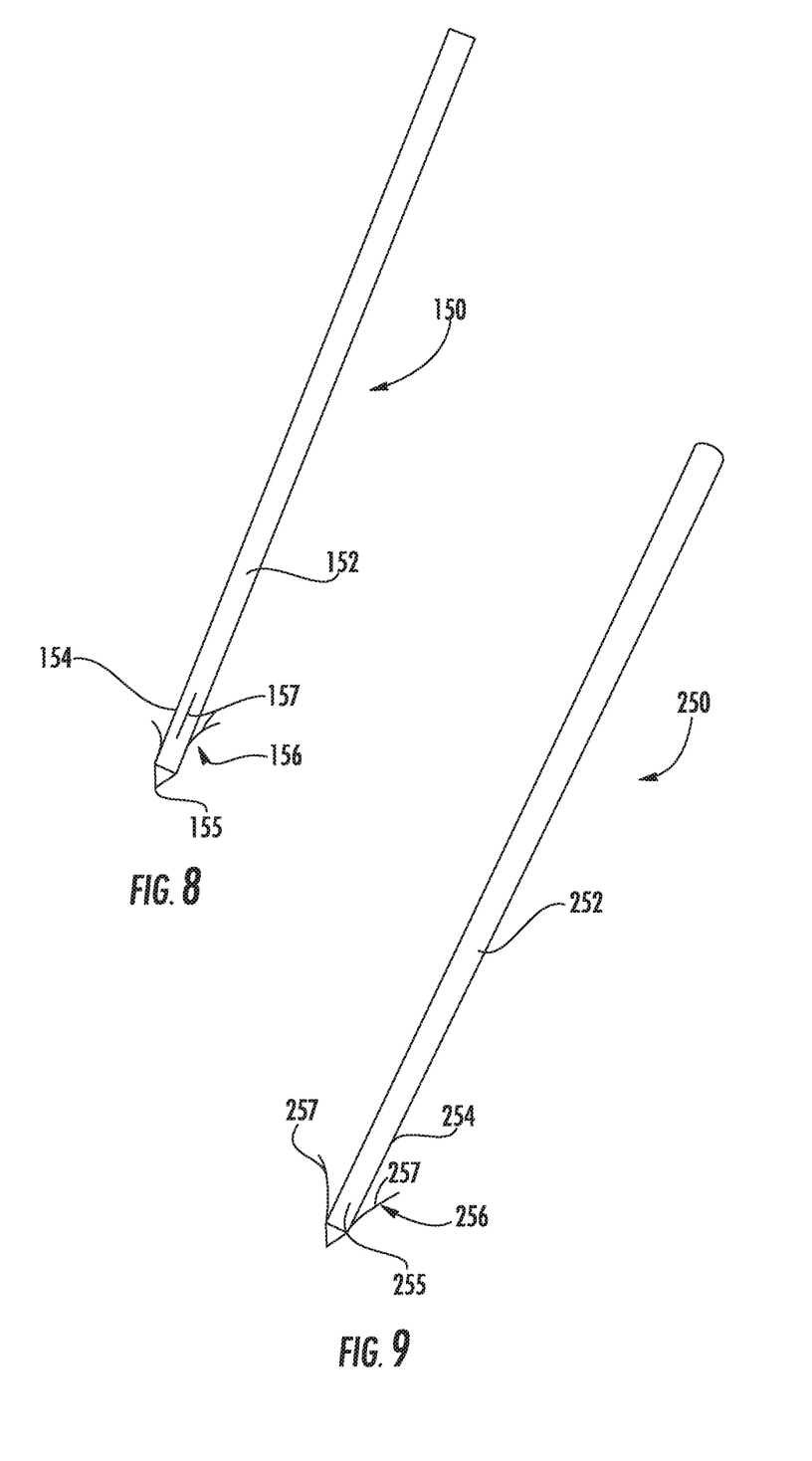
FIG. 8 is a perspective view of the tool of FIG. 7.
FIG. 9 is a perspective view of another tool provided in accordance with the present disclosure.

With reference to FIG. 8, the tool 150 includes a tool shaft 152 and has a distal portion 154. The distal portion 154 includes a barb 156 that has tangs 157 which extend proximally and outward from the distal portion 154 of the tool shaft 152. The tangs 157 of the barb 156 are secured to the distal portion 154 of the tool shaft 152 and spaced apart from a distal tip 155 of the tool shaft 152. Each of the tangs 157 may be secured to the tool shaft 152 at the same point along a longitudinal axis of the tool shaft 152 or may be staggered along the longitudinal axis of the tool shaft 152. The tool 150 may include a sharpened distal tip 155.

In use, the tool 150 is extended or stabbed distally into tissue such that the distal tip 155 pierces the tissue and the barb 156 passes into the tissue. The tangs 157 of the barb 156 may be resiliently flexible inwards such that as the barb 156 moves distally into the tissue, the tangs 157 flex inwards towards the tool shaft 152 and as the tool 150 is moved proximally, the tangs 157 engage the tissue and move outwards such that the tangs 157 prevent the distal portion 154 of the tool 150 from withdrawing from the tissue to draw the tissue proximally together with the tool 150 as shown in FIG. 7.

Referring now to FIG. 9, another tool 250 is provided in accordance with the present disclosure. The tool 250 includes a tool shaft 252 having a distal portion 254. The distal portion 254 includes a barb 256 that has tangs 257 which extend proximally and outward from the distal portion 254 of the tool shaft 252. The tangs 257 of the barb 256 are secured to a distal tip 255 of the tool shaft 252. The distal tip 255 may be blunt or may be sharpened.

In use, the tool 250 is extended or stabbed distally into tissue such that the barb 256 passes into the tissue. The tangs 257 of the barb 256 may be resiliently flexible inwards such that as the barb 256 moves distally into the tissue, the tangs 257 flex inwards towards the tool shaft 252 and as the tool 250 is moved proximally, the tangs 257 engage the tissue and move outwards such that the tangs 257 prevent the distal portion 254 of the tool 250 from withdrawing from the tissue to draw the tissue proximally together with the tool 250.

Figure 10:
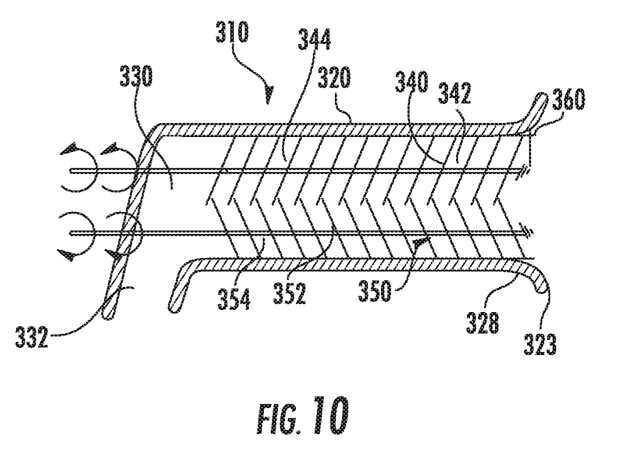
FIG. 10 is a side cross-sectional view of a distal portion of another morcellator provided in accordance with the present disclosure.
Figure 11:
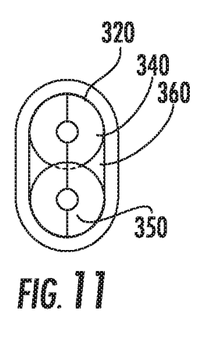
FIG. 11 is a distal end view of the morcellator of FIG. 10.

With reference to FIGS. 10 and 11, another morcellator 310 is provided in accordance with the present disclosure. The morcellator 310 includes an ovular housing 320, a first auger 340, a second auger 350, and an oval knife 360. The ovular housing 320 defines an ovular passage 330 and may include an output channel 332 in communication with a proximal portion of the ovular passage 330. The ovular housing 320 includes a distal portion 328 that houses the knife 360. Specifically, the oval knife 360 is disposed within the ovular passage 330 and extends distally from within the ovular passage 330. The knife 360 is secured to an inner wall of the ovular housing 320 defining the ovular passage 330 such that the knife 360 is fixed relative to the ovular housing 320 and surrounds the ovular passage 330. The ovular housing 320 may include a shield 323 that extends distally beyond the oval knife 360 and/or radially outwardly relative thereto.

The first and second augers 340, 350 each include an auger shaft 342, 352 and a projection or blade 344, 354 extending from the auger shaft 342, 352. The blades 344, 354 are in the form of a screw blade with a pitch configured to draw tissue proximally through the ovular passage 330 as the blades 344, 354 are rotated in a first direction. As shown, the first direction of the blades 344, 354 are opposite one another such that when the blade 344 is rotated clockwise, when viewed from a distal end of the morcellator 310 (FIG. 11), and when the blade 354 is rotated counter-clockwise, when viewed from the distal end of the morcellator 310, the blades 344, 354 draw tissue in contact with the augers 340, 350 proximally through the ovular passage 330. In addition, augers 340, 350 are positioned such that the blades 344, 354 both cross a central longitudinal axis of the housing 320 and overlap but are oriented or windowed with each other such that the blades 344, 354 do not interfere with one another as the augers 340, 350 are rotated. This configuration may morcellate, e.g., tear or rip, tissue in contact with the blades 344, 354 while drawing the tissue proximally through the ovular passage 330.

In use, the shield 323 of the morecellator 310 is brought into contact with tissue to be morcellated and/or removed from a body cavity. The shield 323 may act as a guide to direct the tissue into contact with the augers 340, 350. The housing 320 may be moved distally such that the shield 323 guides tissue into the augers 340, 350. It is contemplated that a tool (not shown) may be used to bring tissue into contact with the augers 340, 350. The tool may be passed through the same or a different opening within a body cavity. It is contemplated, that the tool may be passed through the ovular passage 330 of the housing 320 to draw tissue into contact with the augers 340, 350. The tool may be similar to tool 50 (FIG. 2), tool 150 (FIG. 8), tool 250 (FIG. 9), or may be any other suitable tool.

When the tissue is in contact with the augers 340, 350, the augers 340, 350 are rotated in the first direction such that the augers 340, 350 draw the tissue proximally through the ovular passage 330 and/or morcellate the tissue. The tissue passes through the ovular passage 330 and is expelled through the output channel 332 of the morcellator 310. In addition, as the tissue is drawn into the ovular passage 330, the knife 360 may sever the tissue passing into the ovular passage 330 from a larger piece of tissue to be morcellated. The shield 323 may compress the tissue as the tissue approaches the knife 360 such that tissue larger than the ovular passage 330 may be compressed or reduced before the tissue contacts the knife 360. When the tissue is large, the morcellator 310 may skive the surface of the tissue or may multiple plunges through the tissue to morcellate the entirety of the tissue.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A morcellator comprising:
   a housing defining a longitudinal axis and having an inner wall defining a passage along the longitudinal axis;
   a knife disposed about the inner wall of the housing and secured to a distal portion of the housing, the knife extending distally from the distal portion of the housing;
   a first auger disposed within the housing having a first auger shaft and a first auger blade, the first auger shaft extending in a direction parallel to the longitudinal axis of the housing, the first auger configured to rotate relative to the housing such that the first auger blade moves tissue proximally through the passage; and
   a second auger disposed within the housing and having a second auger shaft and a second auger blade, the second auger shaft parallel to the first auger shaft.

2. The morcellator according to claim 1, wherein a distal end of the first auger is positioned proximal of a distal end of the knife.

3. The morcellator according to claim 1, wherein the housing includes a shield that extends distally beyond the knife.

4. The morcellator according to claim 3, wherein the shield is configured to guide tissue into the passage.

5. The morcellator according to claim 1, wherein the passage of the housing has an ovular cross-section with a first dimension equal to diameters of the first and second augers and a second dimension, perpendicular to the first dimension, less than the sum of the diameters of the first and second augers.

6. The morcellator according to claim 5, wherein the first and second auger blades have opposite pitches such that as the first auger and the second auger are rotated in opposite directions about a respective auger shaft, the first and second augers configured to draw tissue proximally through the passage.

7. The morcellator according to claim 5, wherein the first and second auger blades are windowed relative to one another and positioned such that the longitudinal axis of the housing passes through each of the first and second auger blades.

8. The morcellator according to claim 1, further comprising:
   a third auger having a third auger shaft and a third auger blade, the third auger shaft parallel to the first auger shaft, the third auger positioned adjacent the second auger and on an opposite side of the housing from the first auger; and
   a fourth auger having a fourth auger shaft and a fourth auger blade, the fourth auger shaft parallel to the first auger shaft, the fourth auger positioned adjacent the first and third auger shafts and on an opposite side of the housing from the second auger.

9. The morcellator according to claim 5, wherein the first, second, third, and fourth auger blades are spaced apart from one another and are pitched in the same direction such that rotation of each of the first, second, third, and fourth augers in the same direction about a respective auger shaft is configured to draw tissue proximally through the passage.

10. A method of morcellating tissue using the morcellator of claim 1, the method comprising:
    rotating the housing of the morcellator about the longitudinal axis of the housing; and
    engaging tissue with the first auger to draw tissue proximally through the passage.

11. The method according to claim 10, wherein engaging tissue with the first auger includes passing a tool through the passage to engage tissue distal of the housing and drawing the tissue proximally into the auger.

12. The method according to claim 11, wherein engaging tissue with the tool includes rotating a threaded portion of the tool in a first direction into the tissue and wherein engaging tissue with the first auger includes rotating the auger in a second direction opposite the first direction.

13. The method according to claim 10, wherein rotating the housing includes rotating an elongate shaft extending distally from a handle to rotate the housing, the housing rotatably fixed to a distal portion of the elongate shaft.

14. A morcellator comprising:
    a housing defining a longitudinal axis and having an inner surface defining a passage along the longitudinal axis, the housing including a spiral projection extending inward from the inner surface to form a first auger, the housing configured to rotate about the longitudinal axis such that the auger draws tissue proximally through the passage, wherein the first auger has a first auger shaft;
    a second disposed within the housing and having a second auger shaft, the second auger shaft parallel to the first auger shaft; and a knife secured to a distal portion of the housing.

15. The morcellator according to claim 14, wherein the housing has a proximal end and a distal end, the housing being tapered from the distal end towards the proximal end.

16. The morcellator according to claim 14, further comprising an elongate shaft having a distal portion which supports the housing.

17. The morcellator according to claim 16, wherein the housing is rotatably fixed to the distal portion of the elongate shaft.

18. The morcellator according to claim 16, further comprising a handle, the elongate shaft extending distally from the handle.

19. The morcellator according to claim 18, wherein the handle is configured to rotate the elongate shaft relative to the handle, thereby rotating the housing about the longitudinal axis.

* * * * *